United States Patent
Ichihara et al.

(10) Patent No.: US 10,590,428 B2
(45) Date of Patent: Mar. 17, 2020

(54) SOPHOROLIPID HIGHLY-PRODUCTIVE MUTANT STRAIN

(71) Applicant: KAO CORPORATION, Chuo-ku, Tokyo (JP)

(72) Inventors: Takahiro Ichihara, Wakayama (JP); Yasushi Kageyama, Wakayama (JP); Masatoshi Tohata, Utsunomiya (JP); Fumikazu Takahashi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/740,073

(22) PCT Filed: Jul. 15, 2016

(86) PCT No.: PCT/JP2016/070962
§ 371 (c)(1),
(2) Date: Dec. 27, 2017

(87) PCT Pub. No.: WO2017/014176
PCT Pub. Date: Jan. 26, 2017

(65) Prior Publication Data
US 2018/0208935 A1    Jul. 26, 2018

(30) Foreign Application Priority Data

Jul. 22, 2015   (JP) ................................. 2015-144761

(51) Int. Cl.
| | |
|---|---|
| *C12P 19/44* | (2006.01) |
| *C12N 15/81* | (2006.01) |
| *C12P 19/12* | (2006.01) |
| *C12P 7/64* | (2006.01) |
| *C12N 15/09* | (2006.01) |

(52) U.S. Cl.
CPC .......... *C12N 15/815* (2013.01); *C12N 15/09* (2013.01); *C12P 7/64* (2013.01); *C12P 7/6409* (2013.01); *C12P 19/12* (2013.01)

(58) Field of Classification Search
CPC .............. C12N 1/16; C12N 9/10; C12P 19/44
See application file for complete search history.

(56) References Cited

U.S. PATENT DOCUMENTS

| | | |
|---|---|---|
| 8,530,206 B2 | 9/2013 | Develter et al. |
| 2013/0035403 A1 | 2/2013 | Schaffer et al. |
| 2016/0168612 A1 | 6/2016 | Soetaert et al. |

FOREIGN PATENT DOCUMENTS

| | | |
|---|---|---|
| JP | 2003-009896 A | 1/2003 |
| JP | 2013-511266 A | 4/2013 |
| JP | 2014-150774 A | 8/2014 |
| WO | WO 2012/080116 A1 | 6/2012 |
| WO | WO 2015/028278 A1 | 3/2015 |

OTHER PUBLICATIONS

International Search Report (ISR) for PCT/JP2016/070961; I.A. fd Jul. 15, 2016, dated Oct. 18, 2016 from the Japan Patent Office, Tokyo, Japan.
International Preliminary Report on Patentability (IPRP), Chapter I of the Patent Cooperation Treaty, including the Written Opinion for PCT/JP2016/070961; I.A. fd Jul. 15, 2016, dated Jan. 23, 2018, by the International Bureau of WIPO, Geneva, Switzerland.
Van Bogaert, IN et al., "Microbial production and application of sophorolipids," Appl Microbiol Biotechnol. Aug. 2007;76(1):23-34. Epub May 3, 2007, Springer International, New York, NY.
Zerkowski, JA et al., "Head group-modified sophorolipids: Synthesis of new cationic, zwitterionic, and anionic surfactants," Journal of Surfactants and Detergents. Mar. 2006, vol. 9(1):57-62, AOCS Press, Champaign, IL.
Van Bogaert, IN et al., "Knocking out the MFE-2 gene of *Candida bombicola* leads to improved medium-chain sophorolipid production," FEMS Yeast Res. Jun. 2009;9(4):610-7. doi: 10.1111/j.1567-1364.2009.00501.x. Epub Mar. 17, 2009, Elsevier Science B.V., Amsterdam, Netherlands.
Von Roermund, CWT et al., "Fatty acid metabolism in *Saccharomyces cerevisiae*," Cell Mol Life Sci. Sep. 2003;60(9):1838-51, Birkhauser, Boston, MA.
Ciesielska, K. et al., "SILAC-based proteome analysis of *Starmerella bombicola* sophorolipid production," J Proteome Res. Oct. 4, 2013;12(10):4376-92. doi: 10.1021/pr400392a. Epub Sep. 11, 2013, American Chemical Society, Washington, DC.
Extended European search report including the supplementary European search report and the European search opinion, for EP Application No. 16827736.6, dated Nov. 29, 2018.
Van Bogaert, INA et al., "The biosynthetic gene cluster for sophorolipids: a biotechnological interesting biosurfactant produced by *Starmerella bombicola*," Mol Microbiol. May 2013;88(3):501-9. doi: 10.1111/mmi.12200. Epub Mar. 21, 2013.
Saerens, KMJ et al., "Characterization of sophorolipid biosynthetic enzymes from *Starmerella bombicola*," FEMS Yeast Res. Nov. 2015;15(7). pii: fov075. doi: 10.1093/femsyr/fov075. Epub Aug. 21, 2015, 9 pages.
Claus, S et al., "Sophorolipid production by yeasts: a critical review of the literature and suggestions for future research," Appl Microbiol Biotechnol. Nov. 2017;101(21):7811-7821. doi: 10.1007/s00253-017-8519-7. Epub Sep. 19, 2017.
Saerens, KMJ et al., "One-step production of unacetylated sophorolipids by an acetyltransferase negative *Candida bombicola*," Biotechnol Bioeng. Dec. 2011;108(12):2923-31. doi: 10.1002/bit.23248. Epub Jul. 12, 2011.

*Primary Examiner* — Maryam Monshipouri
(74) *Attorney, Agent, or Firm* — Sterne, Kessler, Goldstein & Fox P.L.L.C.

(57) ABSTRACT

Provided is a microorganism having high sophorolipid production capability. Disclosed is a sophorolipid-producing yeast mutant strain, in which a polypeptide consisting of the amino acid sequence set forth in SEQ ID NO:2 or an amino acid sequence having at least 90% identity therewith, has been deleted or deactivated.

7 Claims, 2 Drawing Sheets
Specification includes a Sequence Listing.

[Figure 1]
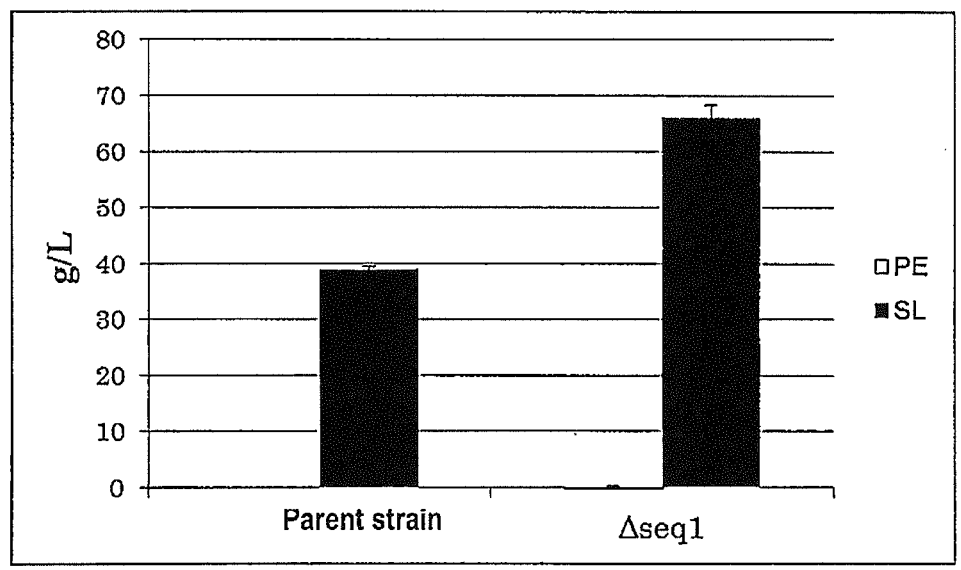
[Figure 2]
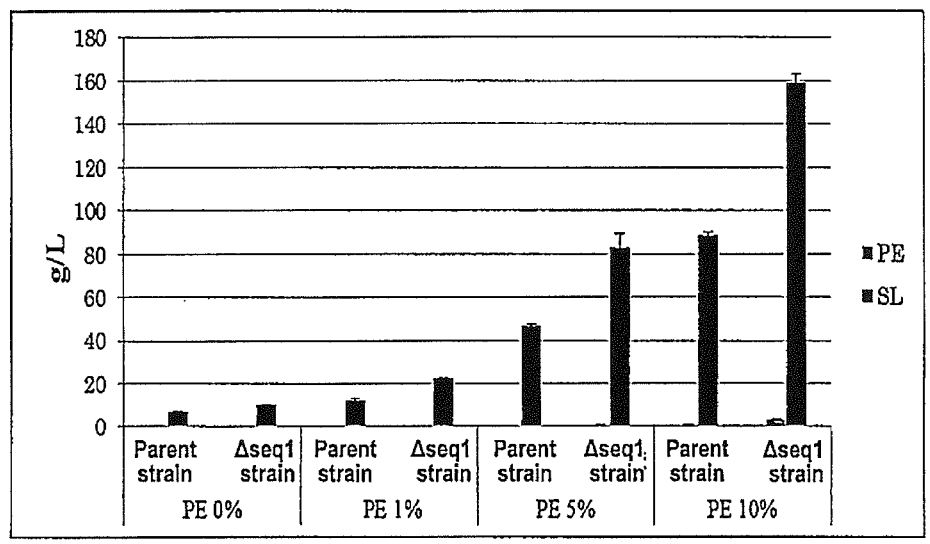

[Figure 3]
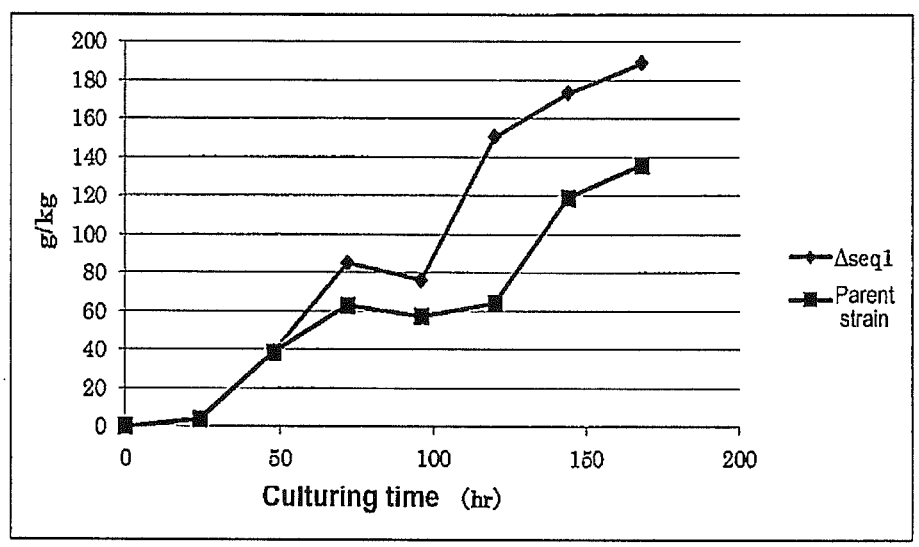

SOPHOROLIPID HIGHLY-PRODUCTIVE MUTANT STRAIN

REFERENCE TO SEQUENCE LISTING SUBMITTED ELECTRONICALLY

The content of the electronically submitted substitute sequence listing, file name 2537-1430001-SeqListing.txt, size 29,467 bytes; and date of creation Apr. 3, 2018, filed herewith, is incorporated herein by reference in its entirety.

IN THE SEQUENCE LISTING

Enter the accompanying computer copy of the sequence listing, file name: 2537-1430001-SeqListing.txt, size 29,467 bytes; and date of creation Apr. 3, 2018, filed electronically herewith, into the application and replace the sequence listing that was filed with the PCT application on Jul. 15, 2016 therewith.

FIELD OF THE INVENTION

The present invention relates to a mutant strain having high sophorolipid productivity, and a method for producing a sophorolipid using the mutant strain.

BACKGROUND OF THE INVENTION

Sophorolipids are glycolipids which are produced by microorganisms, primarily by yeast species and in which long-chain hydroxy fatty acids are bonded to sophorose. Since sophorolipids are amphiphilic lipids having strong surface activity and excellent biodegradability, attention has been paid in recent years to the use of sophorolipids as biosurfactants. Since sophorolipids are products of microorganisms, and nonionic components are main constituents thereof, sophorolipids are highly dermatotropic. Therefore, sophorolipids are used as penetration enhancers for cosmetic products. Furthermore, since sophorolipids have excellent biodegradability and are highly effective even when added in small amounts, the use of sophorolipids is also increasing in the field of cleaning agents such as detergents for dishwashing.

Regarding the yeast species that produces sophorolipids, *Starmerella bombicola* [old name: *Candida bombicola*], which is a non-pathogenic, basidiomycetous yeast, is well known. The sophorolipids produced by *Starmerella bombicola* have a lactone type or acid type structure, have a critical micelle concentration of 40 to 100 mg/L, and decrease the surface tension of water from 72.8 mN/m to 30 mN/m Non Patent Literature 1). Sophorolipids show different physicochemical properties depending on the difference in structure. It has been reported that properties such as antibacterial properties and surface activity vary between the lactone type and the acid type of sophorolipids, or between different fatty acid species that constitute the sophorolipids (Non Patent Literatures 1 and 2).

In a case where sophorolipids are used as cleaning agents or cosmetic materials, competition with the surfactants that are currently used cannot be avoided. Conventionally, since general surfactants are bulk chemical agents, those general surfactants have been produced at very low cost. Therefore, reduction of the production cost of sophorolipids is strongly desired. Furthermore, in order to extend the scope of the usability of sophorolipids, production of sophorolipids having constituent fatty acids with various chain lengths is desirable.

In regard to the production process for sophorolipids, studies and improvements have been hitherto made mainly on, for example, the yield, purification methods, and foaming property-imparting technologies (Patent Literatures 1 and 2). Furthermore, there have been reported methods for producing medium-chain sophorolipids mainly having a carbon chain length of 12, by applying genetic modification to *Starmerella bombicola* and thereby interrupting intracellular β-oxidation metabolism (Non Patent Literature 3, Patent Literature 3). In this genetic modification, MFE 2 (or FOX-2), which is a gene that is in charge of two reactions such as a hydroxylation reaction and a dehydrogenation reaction in β-oxidation of yeast in peroxisomes (Non Patent Literature 4), is deleted, and thereby a β-oxidation reaction is stopped.

(Patent Literature 1) JP 2003-9896 A
(Patent Literature 2) JP 2014-150774 A
(Patent Literature 3) U.S. Pat. No. 8,530,206 B
(Non Patent Literature 1) Appl Microbiol Biotech, 2007, 76(1):23-34.
(Non Patent Literature 2) J SURFACT DETERG, 2006, 9, QTR 1:57-62
(Non Patent Literature 3) FEMS Yeast Res, 2009, 9:610-617
(Non Patent Literature 4) Cell Mol Life Sci, 2003, 60 (9):1838-1851

SUMMARY OF THE INVENTION

The present invention provides a sophorolipid-producing yeast mutant strain, in which a polypeptide consisting of the amino acid sequence set forth in SEQ ID NO:2 or an amino acid sequence having at least 80% identity therewith has been suppressed to be expressed or deactivated.

The present invention also provides a method for producing a sophorolipid-producing yeast mutant strain, the method comprising suppressing expression of or deactivating a polypeptide consisting of the amino acid sequence set forth in SEQ ID NO:2 or an amino acid sequence having at least 80% identity therewith in a sophorolipid-producing yeast.

Furthermore, the present invention provides a method for increasing sophorolipid production capability of a sophorolipid-producing yeast, the method comprising suppressing expression of or deactivating a polypeptide consisting of the amino acid sequence set forth in SEQ ID NO:2 or an amino acid sequence having at least 80% identity therewith in a sophorolipid-producing yeast.

Furthermore, the present invention provides a method for producing a sophorolipid, the method comprising culturing the sophorolipid-producing yeast mutant strain.

BRIEF DESCRIPTION OF THE DRAWINGS

FIG. 1 illustrates an increase of the sophorolipid production capability in a *Starmerella bombicola* mutant strain in which the gene set forth in SEQ ID NO: 1 has been deleted (Δseq1 strain). PE: ethyl palmitate, SL: sophorolipids. Error bar=standard deviation (n=2).

FIG. 2 illustrates the amount of sophorolipid produced by Δseq1 strain under the conditions of different ethyl palmitate concentrations. PE: ethyl palmitate, SL: sophorolipids. Error bar=standard deviation (n=2).

FIG. 3 illustrates the amount of sophorolipid produced by Δseq1 strain in Jar Fermentor culture.

DETAILED DESCRIPTION OF THE INVENTION

The present invention relates to a yeast mutant strain capable of producing sophorolipids with high efficiency, and a method for producing a sophorolipid using the yeast mutant strain.

1. Definition

According to the present specification, the identity of nucleotide sequences and amino acid sequences is calculated according to the Lipman-Pearson method (Science, 1985, 227:1435-1441). Specifically, the identity is calculated by performing an analysis using the homology analysis program (Search Homology) of genetic information processing software, Genetyx-Win (Ver. 5.1.1; Software Development), with the unit size to compare (ktup) being set to 2.

According to the present specification, the phrase "at least 80% identity" in connection with nucleotide sequences and amino acid sequences means identity of 80% or higher, preferably 85% or, higher, more preferably 90% or higher, even more preferably 95% or higher, even more preferably 98% or higher, even more preferably 99% or higher.

According to the present specification, "sophorolipid-producing yeast" refers to a yeast having an capability to produce sophorolipids. Examples of the sophorolipid-producing yeast include Ascomycetes such as the genus *Staermerella*, the genus *Candida*, and the genus *Wickerhamiella*, and preferred examples include *Starmerella bombicola, Candida bogoriensis, Candida batistae, Candida apicola*, and *Wickerhamiella domericqiae*. A more preferred example may be *Starmerella bombicola*.

The polypeptide that is deleted or deactivated in the sophorolipid-producing yeast mutant strain of the present invention is a polypeptide consisting of the amino acid sequence set forth in SEQ ID NO:2, or a polypeptide equivalent thereto. The polypeptide consisting of the amino acid sequence set forth in SEQ ID NO:2 has a Zinc Finger C2H2 type DNA-binding domain respectively at amino acid residues 101 to 123 and 129 to 152, and it is speculated that the polypeptide functions as a transcription factor. As a result of retrieval in the SGD (*Saccharomyces* Genome Database) and Swiss Prot databases, a protein having the highest homology with the polypeptide consisting of the amino acid sequence set forth in SEQ ID NO:2 was a protein having a zinc finger domain and a BTB domain, referred to as *Xenopus tropicalis*-derived ZBTBA; however, the coverage for the amino acid sequence set forth in SEQ ID NO:2 was 11.1%, while the sequence identity was low, such as 39%. The polypeptide consisting of the amino acid sequence set forth in SEQ ID NO:2 may be considered as a novel protein that has not been known hitherto.

According to the present specification, the "polypeptide equivalent to a polypeptide consisting of the amino acid sequence set forth in SEQ ID NO:2" is a polypeptide consisting of an amino acid sequence having at least 80% identity with the amino acid sequence set forth in SEQ ID NO:2. Preferably, the "polypeptide equivalent to a polypeptide consisting of the amino acid sequence set forth in SEQ ID NO: 2 is a putative transcription factor protein, and more preferably a putative transcription factor protein having two Zinc Finger C2H2 type DNA-binding domains.

According to the present specification, the "gene encoding a polypeptide consisting of the amino acid sequence set forth in SEQ ID NO: 2" is preferably a gene consisting of the nucleotide sequence set forth in SEQ ID NO: 1.

According to the present specification, the "gene equivalent to a gene encoding the polypeptide consisting of the amino acid sequence set forth in SEQ ID NO:2" is a gene consisting of a nucleotide sequence having at least 80% identity with the nucleotide sequence set forth in SEQ ID NO:1 and encoding a polypeptide consisting of the amino acid sequence set forth in SEQ ID NO:2 or a polypeptide equivalent thereto.

2. Sophorolipid-Producing Yeast Mutant Strain

The inventors of the present invention found that a sophorolipid-producing yeast in which expression of a polypeptide consisting of the amino acid sequence set forth in SEQ ID NO:2 has been suppressed or the peptide has been deactivated, increases its sophorolipid production capability.

The present invention provides a yeast mutant strain having high sophorolipid production capability. According to the yeast mutant strain of the present invention, sophorolipids can be produced efficiently.

The phorolipid-producing yeast mutant strain of the present invention is a mutant strain in which a polypeptide consisting of the amino acid sequence set forth in SEQ ID NO:2, or a polypeptide equivalent thereto has been deleted or deactivated. Preferably, the sophorolipid-producing yeast mutant strain of the present invention is a mutant strain produced by deleting or deactivating a polypeptide consisting of the amino acid sequence set forth in SEQ ID NO:2, or a polypeptide equivalent thereto, in a sophorolipid-producing yeast by artificial modification.

Preferably, the yeast mutant strain of the present invention is a mutant strain in which expression of a polypeptide consisting of the amino acid sequence set forth in SEQ ID NO:2, or a polypeptide equivalent thereto, is suppressed, as compared to the strain before mutation (parent strain). According to an embodiment, the mutant strain of the present invention may be a mutant strain in which the amount of an expressed polypeptide consisting of the amino acid sequence set forth in SEQ ID NO:2, or polypeptide equivalent thereto, has been decreased to 50% or less, preferably 40% or less, more preferably 30% or less, even more preferably 20% or less, even more preferably 10% or less, even more preferably 5% or less, as compared to the parent strain. The amount of an expressed protein or polypeptide can be measured by a conventionally used method for quantitatively determining expression of a protein, for example, by measurement of the amount of mRNA through quantitative PCR, a colorimetric determination method, a fluorescence method, Western blotting, ELISA, or radioimmunoassay, without being limited to these.

Examples of means for deletion or deactivation of a polypeptide consisting of the amino acid sequence set forth in SEQ ID NO:2, or a polypeptide equivalent thereto, include a method of deleting or deactivating genes encoding those polypeptides, a method of suppressing the translation of mRNA of the genes encoding those polypeptides, and a method of mutating the genes encoding those polypeptides to thereby lower the activity of the polypeptides. Therefore, according to an embodiment, the sophorolipid-producing yeast mutant strain of the present invention is a mutant strain in which a gene encoding a polypeptide consisting of the amino acid sequence set forth in SEQ ID NO:2, or a gene equivalent thereto, has been deleted or deactivated.

Examples of means for deleting or deactivating a gene of a yeast cell include introduction of mutation (deletion, insertion, substitution, or addition) to one or more nucleotides on the nucleotide sequence of the target gene, substitution or insertion of another nucleotide sequence into the nucleotide sequence, or deletion of a portion or the entirety of the nucleotide sequence. Alternatively, similar introduction of mutation, or similar substitution, insertion or deletion of a nucleotide sequence may also be carried out with regard to control regions such as a promoter region of the target gene. For example, the target gene can be deactivated by lowering or eliminating the promoter activity by means of introduction of mutation to a promoter that controls expression of the target gene, or substitution with a promoter of lower expression. Genetic mutation that lowers the activity of a polypeptide can be carried out by, for example, introduction of mutation as described above. The suppression of translation of mRNA can be carried out by, for example, RNA interference using siRNA.

Regarding a specific technique for the introduction of mutation or the substitution, insertion or deletion of a nucleotide sequence, a method for genetic modification of a microorganism that is known in the pertinent art can be used. Examples of the method include, but are not limited to, ultraviolet irradiation, introduction of a site-specific mutation, and homologous recombination method using the SOE-PCR method (splicing by overlap extension PCR; Gene, 1989, 77:61-68).

After the introduction of mutation, or substitution, insertion or deletion of a nucleotide sequence, a genetic analysis is carried out or the amount of an expressed polypeptide encoded by the target gene or the activity thereof is evaluated, and cells having the desired mutation are selected, to thereby obtain the mutant strain of the present invention.

Alternatively, in a case where the means for deleting or deactivating a gene or a control region is the homologous recombination method using SOE-PCR, a mutant strain having the target gene or the control region deleted therefrom can be obtained by incorporating a drug resistance marker gene into a DNA fragment for gene deletion that substitutes the target gene DNA, culturing, on a medium including a drug, cells into which a DNA fragment for deletion has been introduced, and isolating growing colonies. Furthermore, mutation may also be checked by carrying out the genetic analysis or evaluating the amount of the polypeptide expressed or activity of the polypeptide as described above. By following the procedure described above, the yeast mutant strain of the present invention in which a gene encoding a polypeptide consisting of the amino acid sequence set forth in SEQ ID NO:2, or a gene equivalent thereto, has been deleted or deactivated can be obtained.

Alternatively, the yeast mutant strain of the present invention in which a polypeptide consisting of the amino acid sequence set forth in SEQ ID NO: or a polypeptide equivalent thereto has been deleted or deactivated can be obtained by checking increase of the sophorolipid production capability in the yeast mutant strain produced by the procedure described above.

3. Increase of Sophorolipid Production Capability in Mutant Strain

The sophorolipid-producing yeast mutant strain of the present invention that is produced by deleting or deactivating a polypeptide consisting of the amino acid sequence set forth in SEQ ID NO: 2, or a polypeptide equivalent thereto, has increased sophorolipid production capability, as compared to the strain before mutation (parent strain). Therefore, an embodiment of the present invention may be a method for increasing the sophorolipid production capability of a sophorolipid-producing yeast, the method comprising deleting or deactivating a polypeptide consisting of the amino acid sequence set forth in SEQ ID NO:2, or a polypeptide equivalent thereto, in a sophorolipid-producing yeast.

4. Production of Sophorolipids

The sophorolipid-producing yeast mutant strain of the present invention has increased sophorolipid production capability. Furthermore, the sophorolipid-producing yeast mutant strain of the present invention can produce sophorolipids using, for example, hydrocarbon chains and fatty acids having various chain lengths as substrates. Therefore, when the sophorolipid-producing yeast mutant strain of the present invention is cultured together with a substrate having an appropriate chain length, the yeast mutant strain can of efficiently produce a sophorolipid including a constituent fatty acid having a desired chain length. Therefore, the present invention also provides a method for producing a sophorolipid, the method comprising culturing the sophorolipid-producing yeast mutant strain of the present invention.

In the method for producing a sophorolipid of the present invention, the mutant strain of the present invention is cultured in a medium including substrates such as a fatty acid, a fatty acid alkyl ester, an alkane, an alkene, an alkyne, an alcohol, a triacylglycerol, a diacylglycerol, a monoacylglycerol, and a fat or oil. Sophorolipids are collected from the medium after culturing and are appropriately purified as necessary, and thereby sophorolipids can be produced.

Regarding the medium used for the culture, any conventional medium containing a carbon source, a nitrogen source, an inorganic salt, and if necessary, organic trace nutrients such as amino acids and vitamins, can be used. The medium may be any of a synthetic medium and a natural medium.

The carbon source and the nitrogen source included in the medium may be any type of material that can be utilized by the mutant strain to be cultured. Examples of the carbon source include saccharides such as glucose, glycerol, fructose, sucrose, maltose, mannose, galactose, starch hydrolysate, and malt; organic acids such as acetic acid and citric acid; and alcohols such as ethanol. These carbon sources can be used singly or in combination of two or more kinds thereof. Examples of the nitrogen source include ammonia; ammonium salts such as ammonium sulfate, ammonium carbonate, ammonium chloride, ammonium phosphate, and ammonium acetate; and nitrates.

Examples of the inorganic salt include phosphates, magnesium salts, calcium salts, iron salts, and manganese salts. Examples of the organic trace nutrients include amino acids, vitamins, fatty acids, nucleic acids, and peptones, casamino acids, yeast extracts and soybean protein degradation products that contain the amino acids, vitamins, fatty acids, and nucleic acids. In a case where an auxotrophic mutant strain that requires, for example, amino acids for growth is used, it is preferable that the required nutrients are added as supplements.

Preferred examples of the substrate that can be incorporated into the medium include C12-20 fatty acids and alkyl esters thereof, C12-20 alkanes, C12-20 alkenes, C12-20 alkynes, C12-20 alcohols; triacylglycerols, diacylglycerols and monoacylglycerols, each containing C12-20 fatty acids or alkyl esters thereof; and fats or oils containing C12-20 fatty acids or alkyl esters thereof. More preferred examples include C12-18 fatty acids and alkyl esters thereof, C12-18 alkanes, C12-18 alkenes, C12-18 alkynes, C12-18 alcohols; triacylglycerols, diacylglycerols and monoacylglycerols, each containing C12-C18 fatty acids or alkyl esters thereof; and fats or oils containing C12-C18 fatty acids or alkyl esters thereof. Even more preferred examples include C12-C18 fatty acids and alkyl esters thereof.

More specific examples of the substrate, which are not limiter, include, as the C12-20 fatty acids, dodecanoic acid (lauric acid), tridecanoic acid, tetradecanoic acid (myristic acid), pentadecaonic acid (pentadecyl acid), hexadecanoic acid (palmitic acid), hexadecenoic acid, heptadecanoic acid (margaric acid), octadecanoic acid (stearic acid), octadecenoic acid, octadecadienoic acid, octadecatrienoic acid, nonadecanoic acid, eicosanoic acid, eicosadienoic acid, eicosatrienoic acid, and eicosatetraenoic acid; as the C12-20 alkanes, alkenes, alkynes and alcohols, dodecane, tridecane, tetradecane, pentadecane, hexadecane hexadecene, heptadecane, octadecane, octadecene, octadecyne, nonadecane, eicosane, eicosene, eicosyne, dodecanol, tridecanol, tetradecanol, pentadecanol, hexadecanol, hexadecenal, heptadecanol, octadecanol, octadecenol, octadecynol, nonadecanol, and eicosanol; and as the fats or oils containing C12-20 fatty acids or alkyl esters thereof, coconut oil, palm oil, palm kernel oil, olive oil, rapeseed oil, rice bran oil, soybean oil, castor oil, and mahua oil.

Examples of the fatty acid alkyl esters include alkyl esters of the fatty acids mentioned above wherein the alkyl moiety has 1 to 4 carbon atoms, and preferred examples include methyl esters and ethyl esters.

The substrates mentioned above can be used singly or in combination of two or more kinds thereof. Preferably, a fatty acid having any chain length between C12 and C18; an alkyl ester thereof; a triacylglycerol, a diacylglycerol, a monoacylglycerol, or fats or oils, each containing the fatty acid or an alkyl ester thereof, or an alkane, an alkene, an alkyne, or an alcohol, each having any chain length between C12 and 18, is used. More preferably, a fatty acid having any chain length between C12 and C18, or an alkyl ester thereof is used.

The content of the substrate (at the time of initiation of culturing) that can be included in the medium is preferably 1% by mass or more, more preferably 3% by mass or more, even more preferably 5% by mass or more, and is preferably 30% by mass or less, more preferably 20% by mass or less, even more preferably 15% by mass or less. Alternatively, the content is preferably from 1% to 30% by mass, from 1% to 20% by mass, from 1% to 15% by mass, from 3% to 30% by mass, from 3% to 20% by mass, from 3% to 15% by mass, from 5% to 30% by mass, from 5% to 20% by mass, or from 5% to 15% by mass.

The culture conditions may be any conditions in which sophorolipids are fermentatively produced by the mutant strain of the present invention. Culturing is preferably carried out under aerobic conditions, and general methods such as aerated and agitated culture and shaking culture can be applied. The culturing temperature is preferably from 20° C. to 33° C., more preferably from 25° C. to 30° C., even more preferably from 28° C. to 30° C. The initial pH (30° C.) of the medium is preferably from 2 to 7, more preferably from 3 to 6. The culturing time is preferably about from 24 hours to 200 hours, more preferably from 50 to 200 hours.

In regard to the culture described above, sophorolipids may be produced fermentatively by culturing the mutant strain of the present invention under the conditions that enables proliferation of cells, and sophorolipids may also be produced fermentatively by culturing the mutant strain of the present invention in the state of a resting cell, that is, in a state in which growth and proliferation has been stopped.

The method of collecting sophorolipids from the medium after culturing is not particularly limited, and collection may be performed according to any known collecting method. For example, the sophorolipids in the medium can be collected or purified by performing, for example, solvent extraction using, for example, ethyl acetate, fractional precipitation, liquid-liquid partition, column chromatography, high performance liquid chromatography, singly or in appropriate combination.

5. Exemplary Embodiments

As exemplary embodiments of the present invention, for example, the following substances, production methods, use, and methods will be further disclosed in the present specification. However, the present invention is not intended to be limited to these embodiments.

[1] A sophorolipid-producing yeast mutant strain, in which a polypeptide consisting of the amino acid sequence set forth in SEQ ID NO:2 or an amino acid sequence having at least 80% identity with that sequence has been deleted or deactivated.

[2] The mutant strain according to [1], wherein the polypeptide consisting of an amino acid sequence having at least 80% identity with the amino acid sequence set forth in SEQ ID NO:2 is preferably a putative transcription factor protein.

[3] The mutant strain according to [1] or [2], preferably, in which a gene encoding the polypeptide consisting of the amino acid sequence set forth in SEQ ID NO:2, or a gene equivalent thereto has been deleted or deactivated.

[4] The mutant strain according to [3], wherein preferably, the gene encoding the polypeptide consisting of the amino acid sequence set forth in SEQ ID NO:2 is a gene consisting of the nucleotide sequence set forth in SEQ ID NO:1, and the equivalent gene is a gene consisting of the nucleotide sequence having at least 80% identity with the nucleotide sequence set forth in SEQ ID NO:1 and encoding a polypeptide consisting of an amino acid sequence having at least 80% identity with the amino acid sequence set forth in SEQ ID NO:2.

[5] The mutant strain according to any one of [1] to [4], wherein the amount of the expressed polypeptide consisting of the amino acid sequence set forth in SEQ ID NO:2 or an amino acid sequence having at least 80% identity with that sequence, has been decreased to preferably 50% or less, more preferably 40% or less, even more preferably 30% or less, even more preferably 20% or less, even more preferably 10% or less, even more preferably 5% or less, as compared to the parent strain.

[6] The mutant strain according to any one of [1] to [5], wherein the at least 80% identity is identity of preferably 85% or higher, more preferably 90% or higher, even more preferably 95% or higher, even more preferably 98% or higher, even more preferably 99% or higher.

[7] The mutant strain according to any one of [1] to [6], wherein
the sophorolipid-producing yeast is preferably a microorganism of the genus *Starmerella*, more preferably *Starmerella bombicola*.

[8] The mutant strain according to any one of [1] to [7], wherein the mutant strain has increased sophorolipid productivity, as compared to the strain before mutation.

[9] A method for producing a sophorolipid-producing yeast mutant strain, the method comprising deleting or deactivating a polypeptide consisting of the amino acid sequence set forth in SEQ ID NO:2 or an amino acid sequence having at least 80% identity with that sequence, in a sophorolipid-producing yeast.

[10] A method for increasing sophorolipid production capability of a sophorolipid-producing yeast, the method comprising deleting or deactivating a polypeptide consisting of the amino acid sequence set forth in SEQ ID NO:2 or an amino acid sequence having at least 80% identity with that sequence, in a sophorolipid-producing yeast.

[11] The method according to [9] or [10], wherein the polypeptide consisting of an amino acid sequence having at least 80% identity with the amino acid sequence set forth in SEQ ID NO:2 is preferably a putative transcription factor protein.

[12] The method according to any one of [9] to [11], preferably comprising deleting or deactivating a gene encoding the polypeptide consisting of the amino acid sequence set forth in SEQ ID NO:2, or a gene equivalent thereto.

[13] The method according to [12], wherein preferably, the gene encoding the polypeptide consisting of the amino acid sequence set forth in SEQ ID NO:2 is a gene consisting of the nucleotide sequence set forth in SEQ ID NO:1, and the equivalent gene is a gene consisting of a nucleotide sequence having at least 80% identity with the nucleotide sequence set forth in SEQ ID NO:1 and encoding a polypeptide consisting of an amino acid sequence having at least 80% identity with the amino acid sequence set forth in SEQ ID NO:2.

[14] The method according to any one of [9] and [11] to [13], wherein the sophorolipid-producing yeast mutant strain is a strain in which the amount of the expressed polypeptide consisting of the amino acid sequence set forth in SEQ ID NO:2 or an amino acid sequence having at least 80% identity with that sequence, has been decreased to preferably 50% or less, more preferably 40% or less, even more preferably 30% or less, even more preferably 20% or less, even more preferably 10% or less, even more preferably 5% or less, as compared to the parent strain.

[15] The method according to any one of [9] to [14], wherein the at least 80% identity is identity of preferably 85% or higher, more preferably 90% or higher, even more preferably 95% or higher, even more preferably 98% or higher, even more preferably 99% or higher.

[16] The method according to any one of [9] to [15], wherein
the sophorolipid-producing yeast is preferably a microorganism of the genus *Starmerella*, more preferably *Starmerella bombicola*.

[17] The method according to any one of [9] and [11] to [16], wherein the sophorolipid-producing yeast mutant strain is a mutant strain having increased sophorolipid productivity.

[18] A method for producing a sophoroliplid, the method comprising culturing the sophorolipid-producing yeast mutant strain according to any one of [1] to [8].

[19] The method according to [18], wherein a medium for the culturing preferably comprises the following substrate:
at least one substrate selected from the group consisting of C12-C20 fatty acids and alkyl esters thereof, C12-C20 alkanes, C12-C20 alkenes, C12-C20 alkynes, C12-C20 alcohols, triacylglycerols, diacylglycerols and monoacylglycerols, each comprising C12-C20 fatty acids or alkyl esters thereof, and fats or oils comprising C12-C20 fatty acids or alkyl esters thereof;
at least one substrate selected from the group consisting of C12-C18 fatty acids and alkyl esters thereof, C12-C18 alkanes, C12-C18 alkenes, C12-C18 alkynes, C12-C18 alcohols, triacylglycerols, diacylglycerols and monoacylglycerols, each comprising C12-C18 fatty acids or alkyl esters thereof, and fats or oils comprising C12-C18 fatty acids or alkyl esters thereof; or
at least one substrate selected from the group consisting of C12-18 fatty acids and alkyl esters thereof.

[20] The method according to [19], wherein the content of the substrate in the medium is:
preferably 1% by mass or more, more preferably 3% by mass or more, even more preferably 5% by mass or more, and is preferably 30% by mass or less, more preferably 20% by mass or less, even more preferably 15% by mass or less, or
preferably from 1% to 30% by mass, from 1% to 20% by mass, from 1% to 15% by mass, from 3% to 30% by mass, from 3% to 20% by mass, from 3% to 15% by mass, from 5% to 30% by mass, from 5% to 20% by mass, or from 5% to 15% by mass.

[21] The method according to anyone of [18] to [20], wherein the method further comprises collecting sophorolipids from the medium after the culturing.

EXAMPLES

Hereinafter, the present invention will be more specifically described by way of Examples.

Example 1 Production of Gene-Deleted Mutant Strain (1) Establishment of Fragment for Gene Deletion A mutant strain in which a gene consisting of the nucleotide sequence set forth in SEQ ID NO:1 had been deleted was produced by a homologous recombination method using SOE-PCR.

A hygromycin-resistant gene (SEQ ID NO:3) was used for the selection of transformant. A hygromycin-resistant gene fragment was produced by PCR using plasmid loxP-PGK-gb2-hygro-loxP (Gene Bridges) having a hygromycin-resistant gene as a template, and using primers of SEQ ID NO:8 and SEQ ID NO:9. Fragments of a promoter and a terminator of URA3 gene were produced by PCR using the genome of *Starmerella bombicola* as a template, and using primers of SEQ ID NO:10 and SEQ ID NO:11, and primers of SEQ ID NO:12 and SEQ ID NO:13, respectively. The hygromycin-resistant gene fragment was ligated to the promoter fragment and the terminator fragment of URA3 gene by SOE-PCR.

A fragment for deleting the gene set forth in SEQ ID NO:1 was produced. Using the genome of *Starmerella bombicola* as a template, a fragment in the upstream region of the gene set forth in SEQ ID NO:1 was produced by PCR using primers of SEQ ID NO:4 and SEQ ID NO:5, and a fragment in the downstream region was produced by PCR using primers of SEQ ID NO:6 and SEQ ID NO:7. Furthermore, a hygromycin-resistant gene fragment including a promoter fragment and a terminator was produced by PCR using the SOE-PCR product as a template and using primers of SEQ ID NO:10 and SEQ ID NO:13. Three fragments, namely, the upstream region fragment and the downstream region fragment thus obtained, and the hygromycin-resistant gene fragment, were ligated by SOE-PCR. The fragment thus obtained was used as a fragment for deletion of the gene set forth in SEQ ID NO:1.

TABLE 1

| SEQ ID NO. | Primer name | Sequence (5'→3') |
|---|---|---|
| 4 | seq1 upFw | TCCAATTTCTAAGGCGCAAGCGACGCTTCT |
| 5 | seq1 upRv | GTTGCGAGCTGTTTCGAAAATCAATTGGTAAGAGGGAACGCGTAGCGAAG |
| 6 | seq1 doFw | TGTATAGTGACGATGATGAAATTGTTGTCCGAATGCTCTGCGACGGCTCC |
| 7 | seq1 doRv | CAACCCAACGCCTTGACAAGCTTTCCAAAT |
| 8 | Hyg-fw | CACTACTGTAGAGAAATAATATGAAAAAGCCTGAACTCAC |
| 9 | Hyg-re | GAAGGAACTGTTTGAGAAAATTATGAACAAACGACCCAAC |
| 10 | pURA3-fw | TTTTCGAAACAGCTCGCAACGATC |
| 11 | pUra3-re | GTGAGTTCAGGCTTTTTCATATTATTTCTCTACAGTAGTG |
| 12 | tURA3-fw | GTTGGGTCGTTTGTTCATAATTTTCTCAAACAGTTCCTTC |
| 13 | tURA3-re | TTCATCATCGTCACTATACACATC |

(2) Production of Gene Deletion Strain

One platinum loop of *Starmerella bombicola* was inoculated into a 100-mL type test tube containing 5 mL of YPD Broth, and the cells were cultured for 48 hours at 30° C. and 250 rpm. The culture fluid thus obtained was inoculated in an amount of 1% (v/v) into a Sakaguchi flask containing 50 mL of YPD medium, and the cells were cultured at 30° C. and 120 rpm until an OD600 value of 1 to 2 was obtained. The proliferated cells were centrifuged for 5 minutes at 3,000 rpm and 4° C. to collect the cells, and then the cells were washed twice with 20 mL of sterilized water that had been chilled on ice. The cells were suspended in 1 mL of an ice-cooled 1 M sorbitol solution, and the suspension was centrifuged for 5 minutes at 5,000 rpm and 4° C. The supernatant was discarded, subsequently 400 µL of a 1 M sorbitol solution was added to the residue, the mixture was placed on ice, and the mixture was suspended by pipetting. This yeast suspension was dispensed into 50 µL each, and 1 µg of a DNA solution for transformation (including the fragment for deletion of the gene set forth in SEQ ID NO:1) was added to the yeast suspension. The mixture was transferred into an ice-cooled chamber having a 0.2 cm gap. Subsequently, a pulse of 25 µF, 350Ω, and 2.5 kV was applied to the mixture using a GENE PULSER II (Bio-Rad). An ice-cooled 1 M sorbitol-containing YPD Broth was added to the mixture to which a pulse had been applied, the mixture was transferred into a tube having a capacity of 1.5 mL, and the mixture was shaken for 2 hours at 30° C. Subsequently, the mixture was centrifuged for 5 minutes at 5,000 rpm and 4° C., to thereby collect the cells. The cells thus collected were resuspended in 200 µL of a 1 M sorbitol solution, 100 µL each of the suspension was smeared on a selective medium, and the cells were cultured for about one week at 30° C. For the selective medium, an agar medium containing 1% (w/v) of an yeast extract, 2% (w/v) of peptone, 2% (w/v) of glucose, and 500 ppm of hygromycin was used. Colonies that had grown were subjected to colony PCR, it was confirmed that the sequence length amplified from the region of the deletion target gene was changed, and thus a mutant strain in which the gene set forth in SEQ ID NO:1 had been deleted (Δseq1 strain) was obtained.

Example 2 Sophorolipid Productivity of ΔSeq1 Strain (1) Culture of Mutant Strain 5 mL of a medium containing 1% (w/v) of a yeast extract that had been sterilized in advance, 2% (w/v) of peptone, and 2% (w/v) of glucose was introduced into a large-sized test tube, and one platinum loop of any one of the Δseq1 strain obtained in Example 1 and its parent strain was inoculated into the medium. The cells were subjected to shaking culture for 48 hours at 30° C. and 250 rpm, and this was used as a seed culture fluid. The seed culture fluid was inoculated at a concentration of 1% (v/v) into 5 mL of a mixed medium containing 2% (w/v) of a yeast extract, 5% (w/v) of ethyl palmitate, and 12.5% (w/v) of glucose, and shaking culture was carried out for 96 hours at 30° C. and 250 rpm.

(2) Evaluation of Sophorolipid Productivity

After completion of the culturing, ethyl palmitate (PE) and sophorolipids (SL) in the culture fluid were extracted, and the amounts thereof were measured. For the extraction of PE, first, the entire amount of the culture fluid in the large-sized test tube cultured in section (1) was transferred into a Falcon tube (Greiner), subsequently 4 mL of hexane was added to the large-sized test tube and stirred by vortexing for 5 seconds, and the entire amount was transferred to the same Falcon tube. The liquids were thoroughly mixed by vortexing for 5 seconds, and subsequently the liquid was centrifuged for 5 minutes at 3,000 rpm and 25° C. The entire amount of the hexane fraction of the supernatant was collected into a glass tube using a Pasteur pipette. Hexane extraction as described above was repeated once for the remaining liquid, and thereby the entire amount of PE was extracted. For the extraction of SL, 6 mL of ethyl acetate was added to the large-sized test tube that had been used for the culturing in section (1), the mixture was vortexed for 5 seconds, and the entire amount was collected into a Falcon tube. Subsequently, the liquid was centrifuged for 5 minutes at 3,000 rpm and 25° C., and the entire amount of the ethyl acetate fraction of the supernatant was collected into a fresh glass tube using a Pasteur pipette.

Hexane or ethyl acetate was volatilized from the hexane fraction or the ethyl acetate fraction thus collected, by spraying nitrogen gas, and thus dissolved PE or SL was extracted. The difference between the weight of the glass tube containing PE or SL thus extracted, and the weight of the glass tube before collection, was calculated as the amount of PE or the amount of SL in the culture fluid.

The result is presented in FIG. 1. Furthermore, the relative value of sophorolipid productivity of the Δseq1 strain in the case of designating the sophorolipid productivity of the parent strain as 100%, is presented in Table 2. The Δseq1 strain showed increased sophorolipid productivity, as compared to the parent strain.

TABLE 2

| | Relative amount of SL produced |
|---|---|
| Parent strain | 100% |
| Δseq1 strain | 170% |

Example 3 Sophorolipid Productivity of ΔSeq1 Strain Under Conditions of Different Ethyl Palmitate Concentrations Δseq1 strain and its parent strain were cultured by a procedure similar to that of Example 2, and the amounts of ethyl palmitate and sophorolipids in the culture fluid were measured. However, the amount of ethyl palmitate in the mixed medium was adjusted to 0, 1, 5, or 10% (w/v).

The result is presented in FIG. 2. The relative values of sophorolipid productivity of Δseq1 strain in the case of designating the sophorolipid productivity of the parent strain at various ethyl palmitate concentrations as 100%, are presented in Table 3. The Δseq1 strain showed increased sophorolipid productivity, as compared to the parent strain, regardless of the concentration of ethyl palmitate that served as a substrate for sophorolipids. Furthermore, the Δseq1 strain showed higher sophorolipid productivity than the parent strain, even in a medium without any ethyl palmitate added thereto.

Example 4 Sophorolipid Productivity of ΔSeq1 Strain in Jar Fermentor Culture A medium containing 2% (w/v) of a yeast extract that had been sterilized in advance and 1% (w/v) of glucose was introduced into a 30-mL Sakaguchi flask, and one platinum loop of Δseq1 strain obtained in Example 1 or the parent strain was inoculated into the medium. Reciprocal shaking culture was carried out for 48 hours at 30° C. and 120 rpm, and this was used as a seed culture fluid. 1,200 mL of a mixed medium containing 2% (w/v) of an yeast extract, 5% (w/v) of ethyl palmitate, 12.5% (w/v) of glucose, and 0.1% (w/v) of urea was introduced into a 2-L Jar Fermentor incubator, and the seed culture fluid was inoculated into this mixed medium at a concentration of 1% (v/v). Culturing was carried out for 168 hours at 30° C. and 800 rpm. After 96 hours of culturing, 5% (w/v) of ethyl palmitate and 10% (w/v) of glucose were fed into the incubator.

The culture fluid was sampled at a suitable time, and the amounts of ethyl palmitate (PE) and sophorolipids (SL) in the culture fluid were measured. For the measurement of the amount of PE or SL, about 5 mL of the culture fluid was collected into a Falcon tube (Greiner), and then the entire amount of PE or SL was collected in a glass tube by a procedure similar to that of Example 2. The amount of PE or SL per kg of the culture fluid was calculated from the difference between the weights of the glass tube before and after the collection.

The result is presented in FIG. 3. Furthermore, the relative value of sophorolipid productivity of Δseq1 strain at the $168^{th}$ hour of culturing in the case of designating the sophorolipid productivity of the parent strain for the same culturing time as 100%, is presented in Table 4. The Δseq1 strain showed increased sophorolipid productivity, as compared to the parent strain, even in the case of culturing in a large quantity using a Jar Fermentor.

TABLE 3

| | PE0% | PE1% | PE5% | PE10% |
|---|---|---|---|---|
| Parent strain | 100% | 100% | 100% | 100% |
| Δseq1 strain | 151% | 182% | 178% | 180% |

TABLE 4

| | Relative amount of SL produced (at $168^{th}$ hour) |
|---|---|
| Parent strain | 100% |
| Δseq1 strain | 139% |

---

What is claimed is:

1. A sophorolipid-producing yeast mutant strain, in which a gene encoding a polypeptide consisting of the amino acid sequence of SEQ ID NO:2 has been deleted, wherein the sophorolipid-producing yeast is a microorganism of the genus *Starmerella*.

2. The mutant strain according to claim 1, wherein the mutant strain's sophorolipid productivity is greater than that of the mutant strain's parent strain.

3. A method for producing a sophorolipid-producing mutant yeast strain, the method comprising deleting a gene encoding a polypeptide consisting of the amino acid sequence of SEQ ID NO:2 in the sophorolipid-producing yeast strain wherein the sophorolipid-producing yeast is a microorganism of the genus *Starmerella*.

4. A method for increasing the sophorolipid production capability of a parent sophorolipid-producing yeast strain, the method comprising deleting a gene encoding a polypeptide consisting of the amino acid sequence of SEQ ID NO:2 in the parent sophorolipid-producing yeast strain, thereby producing a mutant strain, wherein the sophorolipid production capability of the mutant strain is greater than that of the parent strain and wherein the sophorolipid-producing yeast strain is a microorganism of the genus *Starmerella*.

5. A method for producing a sophorolipid, the method comprising culturing the sophorolipid-producing yeast mutant strain of claim 1.

6. The method according to claim 5, wherein the culturing is in a medium that comprises at least one substrate selected from the group consisting of a C12-C20 fatty acid, an alkyl ester of a C12-C20 fatty acid, a C12-C20 alkane, a C12-C20 alkene, a C12-C20 alkyne, a C12-C20 alcohol, a triacylglycerol, a diacylglycerol, a monoacylglycerol, a fat and an oil wherein the triacylglycerol, diacylglycerol, monoacylglycerol, fat and oil comprise a C12-C20 fatty acid or alkyl ester thereof.

7. The method according to claim 6, wherein the concentration of the substrate in the culture medium at the time of initiation of the culturing is from 1 to 30% (w/v).

* * * * *

SEQUENCE LISTING

```
<160> NUMBER OF SEQ ID NOS: 13

<210> SEQ ID NO 1
<211> LENGTH: 3618
<212> TYPE: DNA
<213> ORGANISM: Starmerella bombicola
<220> FEATURE:
<221> NAME/KEY: CDS
<222> LOCATION: (1)..(3618)

<400> SEQUENCE: 1 atg aca gat ttc gga acc cgc ata gag cac act ttc aca tcc gga ttc      48
Met Thr Asp Phe Gly Thr Arg Ile Glu His Thr Phe Thr Ser Gly Phe
  1               5                  10                  15 gaa ggg ctc agg cgt cag tca gga tcc caa ttc gaa cac att cag ctt      96
Glu Gly Leu Arg Arg Gln Ser Gly Ser Gln Phe Glu His Ile Gln Leu
             20                  25                  30 cac gac tcg cct tct ccc aat ccc gca gtc gct gat ttt agc gct cat     144
His Asp Ser Pro Ser Pro Asn Pro Ala Val Ala Asp Phe Ser Ala His
```

-continued

| | | | | | | | | | | | | | | | | |
|---|---|---|---|---|---|---|---|---|---|---|---|---|---|---|---|---|
| | | 35 | | | | | 40 | | | | | 45 | | | | |
| tcc | act | tgc | atg | gag | gat | tcg | gca | gct | gcc | ggt | ggt | gca | aat | ccc | aag | 192 |
| Ser | Thr | Cys | Met | Glu | Asp | Ser | Ala | Ala | Ala | Gly | Gly | Ala | Asn | Pro | Lys | |
| 50 | | | | | 55 | | | | | 60 | | | | | | |
| gtt | cca | agc | acc | gaa | gaa | ctc | caa | aag | gcc | gca | ggt | gca | cct | ggt | gca | 240 |
| Val | Pro | Ser | Thr | Glu | Glu | Leu | Gln | Lys | Ala | Ala | Gly | Ala | Pro | Gly | Ala | |
| 65 | | | | | 70 | | | | | 75 | | | | | 80 | |
| gct | ggt | agc | gaa | cca | atc | cct | gcc | aaa | tct | ctg | gtg | att | aag | acg | aaa | 288 |
| Ala | Gly | Ser | Glu | Pro | Ile | Pro | Ala | Lys | Ser | Leu | Val | Ile | Lys | Thr | Lys | |
| | | | | 85 | | | | | 90 | | | | | 95 | | |
| aag | cct | agg | cca | tac | gct | tgt | cct | acg | tgc | aca | cgt | agt | ttt | gct | cgt | 336 |
| Lys | Pro | Arg | Pro | Tyr | Ala | Cys | Pro | Thr | Cys | Thr | Arg | Ser | Phe | Ala | Arg | |
| | | | 100 | | | | | 105 | | | | | 110 | | | |
| ttg | gag | cat | ctc | aaa | cgg | cat | gag | cgt | tcc | cac | acc | aag | gag | aaa | ccg | 384 |
| Leu | Glu | His | Leu | Lys | Arg | His | Glu | Arg | Ser | His | Thr | Lys | Glu | Lys | Pro | |
| | | | 115 | | | | | 120 | | | | | 125 | | | |
| ttt | cag | tgt | ccg | gtg | tgt | gag | cgc | agc | ttt | gct | aga | cga | gac | ctt | ctt | 432 |
| Phe | Gln | Cys | Pro | Val | Cys | Glu | Arg | Ser | Phe | Ala | Arg | Arg | Asp | Leu | Leu | |
| | 130 | | | | | 135 | | | | | 140 | | | | | |
| ctg | cgt | cac | aag | caa | aaa | ctc | cat | gcg | tct | ttc | tct | cca | aca | gaa | gaa | 480 |
| Leu | Arg | His | Lys | Gln | Lys | Leu | His | Ala | Ser | Phe | Ser | Pro | Thr | Glu | Glu | |
| 145 | | | | | 150 | | | | | 155 | | | | | 160 | |
| aag | cat | caa | gtc | aag | gac | tca | cag | ttc | ccg | ggc | caa | gta | cct | ctg | gac | 528 |
| Lys | His | Gln | Val | Lys | Asp | Ser | Gln | Phe | Pro | Gly | Gln | Val | Pro | Leu | Asp | |
| | | | | 165 | | | | | 170 | | | | | 175 | | |
| cag | ggt | cct | gtc | cag | tcg | atc | agg | cag | acc | aac | act | gga | tcc | cag | cct | 576 |
| Gln | Gly | Pro | Val | Gln | Ser | Ile | Arg | Gln | Thr | Asn | Thr | Gly | Ser | Gln | Pro | |
| | | | 180 | | | | | 185 | | | | | 190 | | | |
| ctc | agt | caa | cat | ggc | cta | tca | ccc | cta | aat | gcg | agg | gca | atg | gct | cct | 624 |
| Leu | Ser | Gln | His | Gly | Leu | Ser | Pro | Leu | Asn | Ala | Arg | Ala | Met | Ala | Pro | |
| | | | 195 | | | | | 200 | | | | | 205 | | | |
| gcc | aac | gcc | ata | tat | gct | acc | tcg | gca | cgg | ttg | ctg | gca | aat | aat | caa | 672 |
| Ala | Asn | Ala | Ile | Tyr | Ala | Thr | Ser | Ala | Arg | Leu | Leu | Ala | Asn | Asn | Gln | |
| | | 210 | | | | | 215 | | | | | 220 | | | | |
| acc | tcg | tcg | ccc | tct | cct | tcc | gtt | ggc | atg | aac | atg | caa | aac | caa | atg | 720 |
| Thr | Ser | Ser | Pro | Ser | Pro | Ser | Val | Gly | Met | Asn | Met | Gln | Asn | Gln | Met | |
| 225 | | | | | 230 | | | | | 235 | | | | | 240 | |
| gcc | cag | ctc | atg | cag | aac | tac | gaa | ggt | atg | gac | ctg | ctc | act | cct | ctt | 768 |
| Ala | Gln | Leu | Met | Gln | Asn | Tyr | Glu | Gly | Met | Asp | Leu | Leu | Thr | Pro | Leu | |
| | | | | 245 | | | | | 250 | | | | | 255 | | |
| cgc | tcc | acc | tca | cct | tcg | gaa | gct | caa | atg | caa | aat | atg | aat | gct | atg | 816 |
| Arg | Ser | Thr | Ser | Pro | Ser | Glu | Ala | Gln | Met | Gln | Asn | Met | Asn | Ala | Met | |
| | | | 260 | | | | | 265 | | | | | 270 | | | |
| ggt | ggt | ttg | aac | aac | tca | aac | ggc | tac | ata | cct | gct | aca | gat | tcg | ttc | 864 |
| Gly | Gly | Leu | Asn | Asn | Ser | Asn | Gly | Tyr | Ile | Pro | Ala | Thr | Asp | Ser | Phe | |
| | | 275 | | | | | 280 | | | | | 285 | | | | |
| aag | caa | gtc | ttc | cct | cag | cag | act | tcg | ttc | cct | ctg | atg | aac | tcc | cgc | 912 |
| Lys | Gln | Val | Phe | Pro | Gln | Gln | Thr | Ser | Phe | Pro | Leu | Met | Asn | Ser | Arg | |
| | 290 | | | | | 295 | | | | | 300 | | | | | |
| ggt | gaa | aac | aat | ttc | ggt | gag | tgg | agg | cag | ctc | aac | cca | ctc | gca | cac | 960 |
| Gly | Glu | Asn | Asn | Phe | Gly | Glu | Trp | Arg | Gln | Leu | Asn | Pro | Leu | Ala | His | |
| 305 | | | | | 310 | | | | | 315 | | | | | 320 | |
| gag | ctc | gaa | atg | ctt | cat | ggt | gtt | gct | ccc | tca | ttc | aga | gca | gtc | tcg | 1008 |
| Glu | Leu | Glu | Met | Leu | His | Gly | Val | Ala | Pro | Ser | Phe | Arg | Ala | Val | Ser | |
| | | | | 325 | | | | | 330 | | | | | 335 | | |
| aat | cgc | ccc | tct | aga | gcc | agc | tcc | ttc | agt | gct | gct | tca | gct | acc | aca | 1056 |
| Asn | Arg | Pro | Ser | Arg | Ala | Ser | Ser | Phe | Ser | Ala | Ala | Ser | Ala | Thr | Thr | |
| | | | 340 | | | | | 345 | | | | | 350 | | | |
| tac | ctt | cgt | gag | aag | gac | cta | aac | ttg | tac | cca | act | tcg | cag | cag | ttt | 1104 |

```
Tyr Leu Arg Glu Lys Asp Leu Asn Leu Tyr Pro Thr Ser Gln Gln Phe
        355                 360                 365 ggc cag gag gcc tca gag gtc gga ttt gcc act cct cag gcg tac gct    1152
Gly Gln Glu Ala Ser Glu Val Gly Phe Ala Thr Pro Gln Ala Tyr Ala
    370                 375                 380 gtc gat gat gag ggc tac gat ttc gag cca ttg gac ctg aac ttc gtg    1200
Val Asp Asp Glu Gly Tyr Asp Phe Glu Pro Leu Asp Leu Asn Phe Val
385                 390                 395                 400 tcc cca gct cag ttg agc cag ccg ccg ccg cgt aag cgt cgg gtg agc    1248
Ser Pro Ala Gln Leu Ser Gln Pro Pro Pro Arg Lys Arg Arg Val Ser
                405                 410                 415 ctt cat aca tct tcg gca agt cct atg atg aat gcg ttc caa gaa gga    1296
Leu His Thr Ser Ser Ala Ser Pro Met Met Asn Ala Phe Gln Glu Gly
            420                 425                 430 act ccg gcg ata aac cta aat att cag cct caa gga caa agc caa ggg    1344
Thr Pro Ala Ile Asn Leu Asn Ile Gln Pro Gln Gly Gln Ser Gln Gly
            435                 440                 445 cac ctc gat tct cct caa cca gga cct gca atg ctg gca ttg cgg gcc    1392
His Leu Asp Ser Pro Gln Pro Gly Pro Ala Met Leu Ala Leu Arg Ala
    450                 455                 460 caa gca cgt aca cag aga cag ctg tac cag aac cac cac ttt ggc tcg    1440
Gln Ala Arg Thr Gln Arg Gln Leu Tyr Gln Asn His His Phe Gly Ser
465                 470                 475                 480 gga agc gtt gag tct ccg tcg tca ttg agt ttc ttc gaa tcc ggc gac    1488
Gly Ser Val Glu Ser Pro Ser Ser Leu Ser Phe Phe Glu Ser Gly Asp
                485                 490                 495 acc att ggc agt ctg tca gga gtt agc caa agc cca tca cca cag cag    1536
Thr Ile Gly Ser Leu Ser Gly Val Ser Gln Ser Pro Ser Pro Gln Gln
            500                 505                 510 cac ctt gcg aac cag ccg cag cag cct cca agt cag cag cct cca agc    1584
His Leu Ala Asn Gln Pro Gln Gln Pro Pro Ser Gln Gln Pro Pro Ser
            515                 520                 525 cag cag cct cca agc cag cag caa caa act ccg caa aca cag aga cag    1632
Gln Gln Pro Pro Ser Gln Gln Gln Gln Thr Pro Gln Thr Gln Arg Gln
    530                 535                 540 cca gcg tcc agc agg caa cag tcg ttg gac agc ttg ttc tct ggc tta    1680
Pro Ala Ser Ser Arg Gln Gln Ser Leu Asp Ser Leu Phe Ser Gly Leu
545                 550                 555                 560 gat agt tcg ttt gga gag ttt tgt ggg tct cca ggc atg acg cca ggg    1728
Asp Ser Ser Phe Gly Glu Phe Cys Gly Ser Pro Gly Met Thr Pro Gly
                565                 570                 575 ttc acc cct gag atg gcg tcc gga atg acg cct gct ttt act ccc agc    1776
Phe Thr Pro Glu Met Ala Ser Gly Met Thr Pro Ala Phe Thr Pro Ser
            580                 585                 590 atg cac gcc ccg tat cag acc agc atg tcg cct ctt cct gag gaa gcc    1824
Met His Ala Pro Tyr Gln Thr Ser Met Ser Pro Leu Pro Glu Glu Ala
            595                 600                 605 ggt gat atc aaa gac ttt atg gca cag cag aac gac gac ttc gta aac    1872
Gly Asp Ile Lys Asp Phe Met Ala Gln Gln Asn Asp Asp Phe Val Asn
    610                 615                 620 tca tta ttt gac gcc gaa ggt aaa tcg ccc gag ctg cgt aaa agc gga    1920
Ser Leu Phe Asp Ala Glu Gly Lys Ser Pro Glu Leu Arg Lys Ser Gly
625                 630                 635                 640 tac tgt tct gat agt tat acc gat agc agt ggt ttg aat ggg agc cat    1968
Tyr Cys Ser Asp Ser Tyr Thr Asp Ser Ser Gly Leu Asn Gly Ser His
                645                 650                 655 agt ggc agc gcc aat ggc agc ata aac gga agc cac acc ggg aat cat    2016
Ser Gly Ser Ala Asn Gly Ser Ile Asn Gly Ser His Thr Gly Asn His
            660                 665                 670
```

-continued

| | |
|---|---|
| agc gaa agt cac aat gga agt cac cac gga aac ccc aat gga ggt ttt<br>Ser Glu Ser His Asn Gly Ser His His Gly Asn Pro Asn Gly Gly Phe<br>675                                   680                            685 | 2064 |
| cat ggc ggt gta agc ttc ggg att aac gat ctg ggc aac aac act aat<br>His Gly Gly Val Ser Phe Gly Ile Asn Asp Leu Gly Asn Asn Thr Asn<br>690                                   695                          700 | 2112 |
| agc tca ggc agc aat gag gtc agc gga atg cag agg ttc atg gac tct<br>Ser Ser Gly Ser Asn Glu Val Ser Gly Met Gln Arg Phe Met Asp Ser<br>705                                   710                          715                          720 | 2160 |
| tac ttc aac agc ttc gat aca cat ttg tca ttt gtt cac aaa gcc tca<br>Tyr Phe Asn Ser Phe Asp Thr His Leu Ser Phe Val His Lys Ala Ser<br>                         725                          730                          735 | 2208 |
| cag gtc tca cat gcg ctc tct gaa ttc tca tcg acc atc ggc tct cca<br>Gln Val Ser His Ala Leu Ser Glu Phe Ser Ser Thr Ile Gly Ser Pro<br>740                                   745                          750 | 2256 |
| gcc atc tct cct cca tct tcg tcc tcg tct gtt ggc acc acc gcc gac<br>Ala Ile Ser Pro Pro Ser Ser Ser Ser Ser Val Gly Thr Thr Ala Asp<br>                         755                          760                          765 | 2304 |
| aca agt ttg aat gcc aag ctt gct ctc tca caa gca ctg gct gca gtt<br>Thr Ser Leu Asn Ala Lys Leu Ala Leu Ser Gln Ala Leu Ala Ala Val<br>770                                   775                          780 | 2352 |
| gga gcg caa act tta gga gag cgt ggt gaa gct cag gca tat tat tgg<br>Gly Ala Gln Thr Leu Gly Glu Arg Gly Glu Ala Gln Ala Tyr Tyr Trp<br>785                                   790                          795                          800 | 2400 |
| gca gca cgc gac cat aac aac tca gga agt acc act ttg gaa ggg ctg<br>Ala Ala Arg Asp His Asn Asn Ser Gly Ser Thr Thr Leu Glu Gly Leu<br>                         805                          810                          815 | 2448 |
| cag gca gac att tta gtt gcg gta ctt ggt ttg ttc ttc gac gaa cct<br>Gln Ala Asp Ile Leu Val Ala Val Leu Gly Leu Phe Phe Asp Glu Pro<br>820                                   825                          830 | 2496 |
| tct gag cat gca gct tct tta gat aaa ctc acg tca tcg att aca gag<br>Ser Glu His Ala Ala Ser Leu Asp Lys Leu Thr Ser Ser Ile Thr Glu<br>                         835                          840                          845 | 2544 |
| acg gag ttg att atc gct cca cta acg aag tcc cag aac tac tca act<br>Thr Glu Leu Ile Ile Ala Pro Leu Thr Lys Ser Gln Asn Tyr Ser Thr<br>850                                   855                          860 | 2592 |
| tac gat agt ggc cat ggc ctt gga ggc gcc caa tct ctc aaa gtt tct<br>Tyr Asp Ser Gly His Gly Leu Gly Gly Ala Gln Ser Leu Lys Val Ser<br>865                                 870                          875                          880 | 2640 |
| gag gag tgg ccg gct aac gct gag agg ctt tgg gac caa ttt att gcc<br>Glu Glu Trp Pro Ala Asn Ala Glu Arg Leu Trp Asp Gln Phe Ile Ala<br>                         885                          890                          895 | 2688 |
| aac caa tca cgc gtc agg acg ctc cac gca ttg cat gca att tgc tgt<br>Asn Gln Ser Arg Val Arg Thr Leu His Ala Leu His Ala Ile Cys Cys<br>900                                   905                          910 | 2736 |
| tgg gtg cgc aga cca tct cag cag cta cta aac gtt cta gaa tcc tgt<br>Trp Val Arg Arg Pro Ser Gln Gln Leu Leu Asn Val Leu Glu Ser Cys<br>                         915                          920                          925 | 2784 |
| gga tgt gct cca tgc gat gat gac cta tgg aga gca ccc acc agc gac<br>Gly Cys Ala Pro Cys Asp Asp Asp Leu Trp Arg Ala Pro Thr Ser Asp<br>930                                   935                          940 | 2832 |
| att tgg ttg cgg gta gtt gca tcg aaa gaa ctg gat gcg cat cag gtc<br>Ile Trp Leu Arg Val Val Ala Ser Lys Glu Leu Asp Ala His Gln Val<br>945                                   950                          955                          960 | 2880 |
| gcc gaa aca gga ggc aat cct cct cag cag ttc aga atg gtc tta aat<br>Ala Glu Thr Gly Gly Asn Pro Pro Gln Gln Phe Arg Met Val Leu Asn<br>                         965                          970                          975 | 2928 |
| aag ctg cga aat gga gag gtg ccc cag gaa gtt gta tca cag ttt acg<br>Lys Leu Arg Asn Gly Glu Val Pro Gln Glu Val Val Ser Gln Phe Thr<br>980                                   985                          990 | 2976 |

```
tta cag tcg tta ctg tta gct tta gag ctt tcg tgt gac cct gca gaa      3024
Leu Gln Ser Leu Leu Leu Ala Leu Glu Leu Ser Cys Asp Pro Ala Glu
        995                 1000                1005 tac tct ttg cag tct tct agg gca gca ttg agg gcc tgg gaa acg ctt      3072
Tyr Ser Leu Gln Ser Ser Arg Ala Ala Leu Arg Ala Trp Glu Thr Leu
    1010                1015                1020 tgg gct cga agc cca gat gcc tct ctc gat ccc agt cca gag agt ggg      3120
Trp Ala Arg Ser Pro Asp Ala Ser Leu Asp Pro Ser Pro Glu Ser Gly
1025                1030                1035                1040 ccg atc atg agt gat tgt gtc gga att gtg tcg ttg gtt gca ttt tca      3168
Pro Ile Met Ser Asp Cys Val Gly Ile Val Ser Leu Val Ala Phe Ser
                1045                1050                1055 tct ctg aaa atg cgt ggt gtt ctt gat gct ctg tgg caa cat gac ttt      3216
Ser Leu Lys Met Arg Gly Val Leu Asp Ala Leu Trp Gln His Asp Phe
        1060                1065                1070 gct aag gtc agt caa gag gtg tcc aag gct gtc aag gga cag cag tat      3264
Ala Lys Val Ser Gln Glu Val Ser Lys Ala Val Lys Gly Gln Gln Tyr
    1075                1080                1085 agc gcc tcc tca gtc gct aat tat gct gtg gat act ctc gta tgg tgt      3312
Ser Ala Ser Ser Val Ala Asn Tyr Ala Val Asp Thr Leu Val Trp Cys
1090                1095                1100 gag ggt cat gtt tca tcc cat tca atc ttc ttc tct aca ctc ctc gct      3360
Glu Gly His Val Ser Ser His Ser Ile Phe Phe Ser Thr Leu Leu Ala
1105                1110                1115                1120 gtt tcg gag tgt ggg ctg gtg ctt gcc gag tcc cta cgg ctc atc atc      3408
Val Ser Glu Cys Gly Leu Val Leu Ala Glu Ser Leu Arg Leu Ile Ile
                1125                1130                1135 tcg aaa aac acg cca act agc aac gca gag gag cag ctt atc caa cga      3456
Ser Lys Asn Thr Pro Thr Ser Asn Ala Glu Glu Gln Leu Ile Gln Arg
        1140                1145                1150 agc agg aaa ctt gtg agt aca gtg ctc aaa gta tcg ccc tct gcc gac      3504
Ser Arg Lys Leu Val Ser Thr Val Leu Lys Val Ser Pro Ser Ala Asp
    1155                1160                1165 ctc gag atg ctt ccc aat cac gtt ctg aga gct gct gtg tgc ttg att      3552
Leu Glu Met Leu Pro Asn His Val Leu Arg Ala Ala Val Cys Leu Ile
1170                1175                1180 aga ctg agc gac tgg cct ctt gtt ggt gct ctt tct cgc atg ctg ctt      3600
Arg Leu Ser Asp Trp Pro Leu Val Gly Ala Leu Ser Arg Met Leu Leu
1185                1190                1195                1200 ggt cac ctg tcg act tga                                              3618
Gly His Leu Ser Thr
                1205

<210> SEQ ID NO 2
<211> LENGTH: 1205
<212> TYPE: PRT
<213> ORGANISM: Starmerella bombicola

<400> SEQUENCE: 2

Met Thr Asp Phe Gly Thr Arg Ile Glu His Thr Phe Thr Ser Gly Phe
1               5                   10                  15

Glu Gly Leu Arg Arg Gln Ser Gly Ser Gln Phe Glu His Ile Gln Leu
            20                  25                  30

His Asp Ser Pro Ser Pro Asn Pro Ala Val Ala Asp Phe Ser Ala His
        35                  40                  45

Ser Thr Cys Met Glu Asp Ser Ala Ala Ala Gly Gly Ala Asn Pro Lys
    50                  55                  60

Val Pro Ser Thr Glu Glu Leu Gln Lys Ala Ala Gly Ala Pro Gly Ala
65                  70                  75                  80
```

```
Ala Gly Ser Glu Pro Ile Pro Ala Lys Ser Leu Val Ile Lys Thr Lys
                 85                  90                  95

Lys Pro Arg Pro Tyr Ala Cys Pro Thr Cys Thr Arg Ser Phe Ala Arg
            100                 105                 110

Leu Glu His Leu Lys Arg His Glu Arg Ser His Thr Lys Glu Lys Pro
        115                 120                 125

Phe Gln Cys Pro Val Cys Glu Arg Ser Phe Ala Arg Arg Asp Leu Leu
    130                 135                 140

Leu Arg His Lys Gln Lys Leu His Ala Ser Phe Ser Pro Thr Glu Glu
145                 150                 155                 160

Lys His Gln Val Lys Asp Ser Gln Phe Pro Gly Gln Val Pro Leu Asp
                165                 170                 175

Gln Gly Pro Val Gln Ser Ile Arg Gln Thr Asn Thr Gly Ser Gln Pro
            180                 185                 190

Leu Ser Gln His Gly Leu Ser Pro Leu Asn Ala Arg Ala Met Ala Pro
        195                 200                 205

Ala Asn Ala Ile Tyr Ala Thr Ser Ala Arg Leu Leu Ala Asn Asn Gln
    210                 215                 220

Thr Ser Pro Ser Pro Ser Val Gly Met Asn Met Gln Asn Gln Asn Met
225                 230                 235                 240

Ala Gln Leu Met Gln Asn Tyr Glu Gly Met Asp Leu Leu Thr Pro Leu
                245                 250                 255

Arg Ser Thr Ser Pro Ser Glu Ala Gln Met Gln Asn Met Asn Ala Met
            260                 265                 270

Gly Gly Leu Asn Asn Ser Asn Gly Tyr Ile Pro Ala Thr Asp Ser Phe
        275                 280                 285

Lys Gln Val Phe Pro Gln Gln Thr Ser Phe Pro Leu Met Asn Ser Arg
    290                 295                 300

Gly Glu Asn Asn Phe Gly Glu Trp Arg Gln Leu Asn Pro Leu Ala His
305                 310                 315                 320

Glu Leu Glu Met Leu His Gly Val Ala Pro Ser Phe Arg Ala Val Ser
                325                 330                 335

Asn Arg Pro Ser Arg Ala Ser Ser Phe Ser Ala Ala Ser Ala Thr Thr
            340                 345                 350

Tyr Leu Arg Glu Lys Asp Leu Asn Leu Tyr Pro Thr Ser Gln Gln Phe
        355                 360                 365

Gly Gln Glu Ala Ser Glu Val Gly Phe Ala Thr Pro Gln Ala Tyr Ala
    370                 375                 380

Val Asp Asp Glu Gly Tyr Asp Phe Glu Pro Leu Asp Leu Asn Phe Val
385                 390                 395                 400

Ser Pro Ala Gln Leu Ser Gln Pro Pro Arg Lys Arg Arg Val Ser
                405                 410                 415

Leu His Thr Ser Ser Ala Ser Pro Met Met Asn Ala Phe Gln Glu Gly
            420                 425                 430

Thr Pro Ala Ile Asn Leu Asn Ile Gln Pro Gln Gly Gln Ser Gln Gly
        435                 440                 445

His Leu Asp Ser Pro Gln Pro Gly Pro Ala Met Leu Ala Leu Arg Ala
    450                 455                 460

Gln Ala Arg Thr Gln Arg Gln Leu Tyr Gln Asn His His Phe Gly Ser
465                 470                 475                 480

Gly Ser Val Glu Ser Pro Ser Ser Leu Ser Phe Phe Glu Ser Gly Asp
                485                 490                 495
```

-continued

Thr Ile Gly Ser Leu Ser Gly Val Ser Gln Ser Pro Ser Pro Gln Gln
            500                 505                 510

His Leu Ala Asn Gln Pro Gln Gln Pro Pro Ser Gln Gln Pro Pro Ser
            515                 520                 525

Gln Gln Pro Pro Ser Gln Gln Gln Thr Pro Gln Thr Gln Arg Gln
    530                 535                 540

Pro Ala Ser Ser Arg Gln Gln Ser Leu Asp Ser Leu Phe Ser Gly Leu
545                 550                 555                 560

Asp Ser Ser Phe Gly Glu Phe Cys Gly Ser Pro Gly Met Thr Pro Gly
                565                 570                 575

Phe Thr Pro Glu Met Ala Ser Gly Met Thr Pro Ala Phe Thr Pro Ser
            580                 585                 590

Met His Ala Pro Tyr Gln Thr Ser Met Ser Pro Leu Pro Glu Glu Ala
            595                 600                 605

Gly Asp Ile Lys Asp Phe Met Ala Gln Gln Asn Asp Asp Phe Val Asn
            610                 615                 620

Ser Leu Phe Asp Ala Glu Gly Lys Ser Pro Glu Leu Arg Lys Ser Gly
625                 630                 635                 640

Tyr Cys Ser Asp Ser Tyr Thr Asp Ser Ser Gly Leu Asn Gly Ser His
                645                 650                 655

Ser Gly Ser Ala Asn Gly Ser Ile Asn Gly Ser His Thr Gly Asn His
            660                 665                 670

Ser Glu Ser His Asn Gly Ser His Gly Asn Pro Asn Gly Gly Phe
            675                 680                 685

His Gly Gly Val Ser Phe Gly Ile Asn Asp Leu Gly Asn Asn Thr Asn
            690                 695                 700

Ser Ser Gly Ser Asn Glu Val Ser Gly Met Gln Arg Phe Met Asp Ser
705                 710                 715                 720

Tyr Phe Asn Ser Phe Asp Thr His Leu Ser Phe Val His Lys Ala Ser
                725                 730                 735

Gln Val Ser His Ala Leu Ser Glu Phe Ser Ser Thr Ile Gly Ser Pro
            740                 745                 750

Ala Ile Ser Pro Pro Ser Ser Ser Ser Val Gly Thr Thr Ala Asp
            755                 760                 765

Thr Ser Leu Asn Ala Lys Leu Ala Leu Ser Gln Ala Leu Ala Ala Val
    770                 775                 780

Gly Ala Gln Thr Leu Gly Glu Arg Gly Glu Ala Gln Ala Tyr Tyr Trp
785                 790                 795                 800

Ala Ala Arg Asp His Asn Asn Ser Gly Ser Thr Thr Leu Glu Gly Leu
            805                 810                 815

Gln Ala Asp Ile Leu Val Ala Val Leu Gly Leu Phe Phe Asp Glu Pro
            820                 825                 830

Ser Glu His Ala Ala Ser Leu Asp Lys Leu Thr Ser Ser Ile Thr Glu
            835                 840                 845

Thr Glu Leu Ile Ile Ala Pro Leu Thr Lys Ser Gln Asn Tyr Ser Thr
    850                 855                 860

Tyr Asp Ser Gly His Gly Leu Gly Gly Ala Gln Ser Leu Lys Val Ser
865                 870                 875                 880

Glu Glu Trp Pro Ala Asn Ala Glu Arg Leu Trp Asp Gln Phe Ile Ala
                885                 890                 895

Asn Gln Ser Arg Val Arg Thr Leu His Ala Leu His Ala Ile Cys Cys
            900                 905                 910

Trp Val Arg Arg Pro Ser Gln Gln Leu Leu Asn Val Leu Glu Ser Cys

```
                915                 920                 925
    Gly Cys Ala Pro Cys Asp Asp Asp Leu Trp Arg Ala Pro Thr Ser Asp
        930                 935                 940
    Ile Trp Leu Arg Val Val Ala Ser Lys Glu Leu Asp Ala His Gln Val
    945                 950                 955                 960
    Ala Glu Thr Gly Gly Asn Pro Pro Gln Gln Phe Arg Met Val Leu Asn
                    965                 970                 975
    Lys Leu Arg Asn Gly Glu Val Pro Gln Glu Val Val Ser Gln Phe Thr
                980                 985                 990
    Leu Gln Ser Leu Leu Leu Ala Leu Glu Leu Ser Cys Asp Pro Ala Glu
            995                 1000                1005
    Tyr Ser Leu Gln Ser Ser Arg Ala Ala Leu Arg Ala Trp Glu Thr Leu
        1010                1015                1020
    Trp Ala Arg Ser Pro Asp Ala Ser Leu Asp Pro Ser Pro Glu Ser Gly
    1025                1030                1035                1040
    Pro Ile Met Ser Asp Cys Val Gly Ile Val Ser Leu Val Ala Phe Ser
                    1045                1050                1055
    Ser Leu Lys Met Arg Gly Val Leu Asp Ala Leu Trp Gln His Asp Phe
                1060                1065                1070
    Ala Lys Val Ser Gln Glu Val Ser Lys Ala Val Lys Gly Gln Gln Tyr
            1075                1080                1085
    Ser Ala Ser Ser Val Ala Asn Tyr Ala Val Asp Thr Leu Val Trp Cys
        1090                1095                1100
    Glu Gly His Val Ser Ser His Ser Ile Phe Phe Ser Thr Leu Leu Ala
    1105                1110                1115                1120
    Val Ser Glu Cys Gly Leu Val Leu Ala Glu Ser Leu Arg Leu Ile Ile
                    1125                1130                1135
    Ser Lys Asn Thr Pro Thr Ser Asn Ala Glu Glu Gln Leu Ile Gln Arg
                1140                1145                1150
    Ser Arg Lys Leu Val Ser Thr Val Leu Lys Val Ser Pro Ser Ala Asp
            1155                1160                1165
    Leu Glu Met Leu Pro Asn His Val Leu Arg Ala Ala Val Cys Leu Ile
        1170                1175                1180
    Arg Leu Ser Asp Trp Pro Leu Val Gly Ala Leu Ser Arg Met Leu Leu
    1185                1190                1195                1200
    Gly His Leu Ser Thr
                1205

<210> SEQ ID NO 3
<211> LENGTH: 1026
<212> TYPE: DNA
<213> ORGANISM: Escherichia coli

<400> SEQUENCE: 3
atgaaaaagc ctgaactcac cgcgacgtct gtcgagaagt ttctgatcga aaagttcgac     60
agcgtctccg acctgatgca gctctcggag ggcgaagaat ctcgtgcttt cagcttcgat    120
gtaggagggc gtggatacgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg cccattcgg accgcaagga    420 atcggtcaat acactacatg gcgtgatttc atatgcgcga ttgctgatcc ccatgtgtat    480
```

```
cactggcaaa ctgtgatgga cgacaccgtc agtgcgtccg tcgcgcaggc tctcgatgag      540
ctgatgcttt gggccgagga ctgccccgaa gtccggcacc tcgtgcacgc ggatttcggc      600
tccaacaatg tcctgacgga caatggccgc ataacagcgg tcattgactg gagcgaggcg      660
atgttcgggg attcccaata cgaggtcgcc aacatcttct tctggaggcc gtggttggct      720
tgtatggagc agcagacgcg ctacttcgag cggaggcatc cggagcttgc aggatcgccg      780
cggctccggg cgtatatgct ccgcattggt cttgaccaac tctatcagag cttggttgac      840
ggcaatttcg atgatgcagc ttgggcgcag ggtcgatgcg acgcaatcgt ccgatccgga      900
gccgggactg tcgggcgtac acaaatcgcc cgcagaagcg cggccgtctg gaccgatggc      960
tgtgtagaag tacttgccga tagtggaaac cgacgcccca gcactcgtcc gagggcaaag     1020
gaatag                                                                1026
```

<210> SEQ ID NO 4
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 4
tccaatttct aaggcgcaag cgacgcttct                                        30

<210> SEQ ID NO 5
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 5
gttgcgagct gtttcgaaaa tcaattggta agagggaacg cgtagcgaag                  50

<210> SEQ ID NO 6
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 6
tgtatagtga cgatgatgaa attgttgtcc gaatgctctg cgacggctcc                  50

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 7
caacccaacg ccttgacaag ctttccaaat                                        30

<210> SEQ ID NO 8
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 8

```
cactactgta gagaaataat atgaaaaagc ctgaactcac                              40

<210> SEQ ID NO 9
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 9
gaaggaactg tttgagaaaa ttatgaacaa acgacccaac                              40

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 10
ttttcgaaac agctcgcaac gatc                                               24

<210> SEQ ID NO 11
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 11
gtgagttcag gcttttttcat attatttctc tacagtagtg                             40

<210> SEQ ID NO 12
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 12
gttgggtcgt tgttcataa ttttctcaaa cagttccttc                               40

<210> SEQ ID NO 13
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 13
ttcatcatcg tcactataca catc                                               24
```